(12) United States Patent
Baba et al.

(10) Patent No.: US 9,538,990 B2
(45) Date of Patent: Jan. 10, 2017

(54) ULTRASONIC DIAGNOSTIC APPARATUS AND ULTRASONIC DIAGNOSTIC APPARATUS CONTROL METHOD

(71) Applicant: TOSHIBA MEDICAL SYSTEMS CORPORATION, Otawara-shi, Tochigi-ken (JP)

(72) Inventors: Tatsuro Baba, Otawara (JP); Cong Yao, Otawara (JP); Go Tanaka, Otawara (JP); Isao Uchiumi, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 188 days.

(21) Appl. No.: 13/946,205

(22) Filed: Jul. 19, 2013

(65) Prior Publication Data

US 2013/0303908 A1    Nov. 14, 2013

Related U.S. Application Data

(63) Continuation of application No. 13/108,314, filed on May 16, 2011, now abandoned.

(30) Foreign Application Priority Data

May 19, 2010    (JP) .................................. 2010-115547

(51) Int. Cl.
*A61B 8/13*    (2006.01)
*A61B 8/08*    (2006.01)
(Continued)

(52) U.S. Cl.
CPC .............. *A61B 8/5246* (2013.01); *A61B 8/06* (2013.01); *A61B 8/13* (2013.01); *A61B 8/463* (2013.01);
(Continued)

(58) Field of Classification Search
CPC ............. A61B 8/06; A61B 8/13; A61B 8/463; A61B 8/5246; G01S 15/8979; G01S 7/52034; G01S 7/52066; G01S 7/52074
See application file for complete search history.

(56) References Cited

U.S. PATENT DOCUMENTS

| 4,559,952 A | 12/1985 | Angelsen et al. |
| 5,642,732 A | 7/1997 | Wang |

(Continued)

FOREIGN PATENT DOCUMENTS

| CN | 101336830 A | 1/2009 |
| CN | 101449984 A | 6/2009 |

(Continued)

OTHER PUBLICATIONS

EP Extended Search Report for corresponding EP Application No. 11250533.4 mailed on Sep. 9, 2011.

(Continued)

*Primary Examiner* — Mark Remaly
(74) *Attorney, Agent, or Firm* — Kenichiro Yoshida (57) ABSTRACT

According to one embodiment, an ultrasonic diagnostic apparatus is configured to execute an imaging mode of alternately executing a continuous wave Doppler mode of acquiring time-series Doppler data by performing continuous wave transmission/reception with respect to an object and a B mode of acquiring tomogram data represented by luminance by transmitting and receiving a pulse wave to and from the object, the apparatus includes a data acquisition unit configured to acquire continuous wave Doppler data and the tomogram data by alternately executing the continuous wave Doppler mode and the B mode while switching the modes, and a display unit configured to simultaneously display Doppler spectrum information generated based on the continuous wave Doppler data and a tomogram generated based on the tomogram data.

9 Claims, 8 Drawing Sheets

(51) Int. Cl.
*A61B 8/06* (2006.01)
*A61B 8/00* (2006.01)
*G01S 7/52* (2006.01)
*G01S 15/89* (2006.01)

(52) U.S. Cl.
CPC ........ *G01S 7/52034* (2013.01); *G01S 7/52074* (2013.01); *G01S 15/8979* (2013.01); *G01S 7/52066* (2013.01)

(56) References Cited

U.S. PATENT DOCUMENTS

| | | | |
|---|---|---|---|
| 6,110,113 | A | 8/2000 | Banjamin et al. |
| 6,251,077 | B1 | 6/2001 | Mo et al. |
| 2002/0173721 | A1 | 11/2002 | Grunwald et al. |
| 2005/0203401 | A1* | 9/2005 | Takimoto ..................... 600/441 |
| 2009/0149759 | A1 | 6/2009 | Baba et al. |

FOREIGN PATENT DOCUMENTS

| | | |
|---|---|---|
| EP | 0 222 913 A1 | 5/1987 |
| EP | 0 475 100 A1 | 3/1992 |
| JP | 2615519 B2 | 1/1993 |
| JP | 3642834 B2 | 2/1997 |
| JP | 2001-149370 A | 6/2001 |

OTHER PUBLICATIONS

CN Office Action with English translation for CN Application No. 201110169347.5 mailed on Dec. 20, 2012.

* cited by examiner

ULTRASONIC DIAGNOSTIC APPARATUS AND ULTRASONIC DIAGNOSTIC APPARATUS CONTROL METHOD

CROSS-REFERENCE TO RELATED APPLICATIONS

This application is based upon and claims the benefit of priority from Japanese Patent Application No. 2010-115547, filed May 19, 2010; the entire contents of which are incorporated herein by reference.

FIELD

Embodiments described herein relate generally to an ultrasonic diagnostic apparatus and an ultrasonic diagnostic apparatus control method.

BACKGROUND

The present application relates to an ultrasonic diagnostic apparatus which can execute a continuous wave Doppler (CWD)/B simultaneous mode of simultaneously displaying a Doppler spectrum image captured by CWD and a tomogram captured by the B mode in cardiac diagnosis.

Ultrasonic diagnosis allows to display in real time how the heart beats or the fetus moves, by simply bringing an ultrasonic probe into contact with the body surface. This technique is highly safe, and hence allows repetitive examination. Furthermore, this system is smaller in size than other diagnostic apparatuses such as X-ray, CT, and MRI apparatuses and can be moved to the bedside to be easily and conveniently used for examination. In addition, ultrasonic diagnosis is free from the influences of exposure using X-rays and the like, and hence can be used in obstetric treatment, treatment at home, and the like.

Recently, in cardiac diagnosis, image diagnosis called PWD (Pulse Wave Doppler)/B simultaneous mode has been executed by using such an ultrasonic diagnostic apparatus. The PWD/B simultaneous mode is a mode of executing Doppler spectrum imaging by continuous wave Doppler and B-mode tomography at a predetermined timing and displaying the captured images in real time. The PWD/B simultaneous mode includes an imaging method called interleaved scan and an imaging method called segment scan. Interleaved scan is a technique of repeatedly executing, for example, one B-mode scan per four times of execution of Doppler scan. Segment scan is a technique of alternately repeating a period (Doppler segment period) of repeating transmission/reception in the Doppler mode by a predetermined number of times and a period (non-Doppler segment period) of repeating transmission/reception in the B mode by a predetermined number of times.

The CWD/B simultaneous mode, however, requires switching of continuous waves unlike a case in which PWD is used. For this reason, a B-mode image is displayed in the freeze mode during a period in which real-time display is performed in the Doppler mode. This makes it difficult to simultaneously implement real-time display of both a Doppler spectrum and a B-mode image in the CWD/B simultaneous mode, although the implementation of such technique is clinically demanded.

In order to improve the real-time performance of the CWD/B simultaneous mode, it is necessary to solve, for example, the following two problems. One is the problem of losses in intermittent execution of continuous STFT (Short Time Fourier Transform) analysis. For example, a large loss of about 50 ms occurs per frame in B-mode images. Even if interpolation of a loss of a maximum of about 16 ms is performed for this loss, the problem of image quality deterioration occurs. The other is the problem of strong transient responses (30 ms to 100 ms) due to the necessity to instantly switch B-mode scan and Doppler-mode scan. This transient response causes noise such as spike noise in a Doppler spectrum, resulting in degrade of image quality.

It is possible to handle the problem of losses in intermittent execution of continuous STFT analysis by using the spectrum loss interpolation technique disclosed in, for example, Jpn. Pat. Appln. KOKAI Publication No. 2001-149370, which uses an ARX model using an ECG waveform as a deterministic external input. However, there is no corresponding unit for the other problem of transient responses.

DETAILED DESCRIPTION

In general, according to one embodiment, an ultrasonic diagnostic apparatus is configured to execute an imaging mode of alternately executing a continuous wave Doppler mode of acquiring time-series Doppler data by performing continuous wave transmission/reception with respect to an object and a B mode of acquiring tomogram data represented by luminance by transmitting and receiving a pulse wave to and from the object, the apparatus comprising: a data acquisition unit configured to acquire continuous wave Doppler data and the tomogram data by alternately executing the continuous wave Doppler mode and the B mode while switching the modes; and a display unit configured to simultaneously display Doppler spectrum information generated based on the continuous wave Doppler data and a tomogram generated based on the tomogram data.

The embodiments will be described below with reference to the views of the accompanying drawing. Note that the same reference numerals in the following description denote constituent elements having almost the same functions and arrangements, and a repetitive description will be made only when required.

First Embodiment

Figure 1:
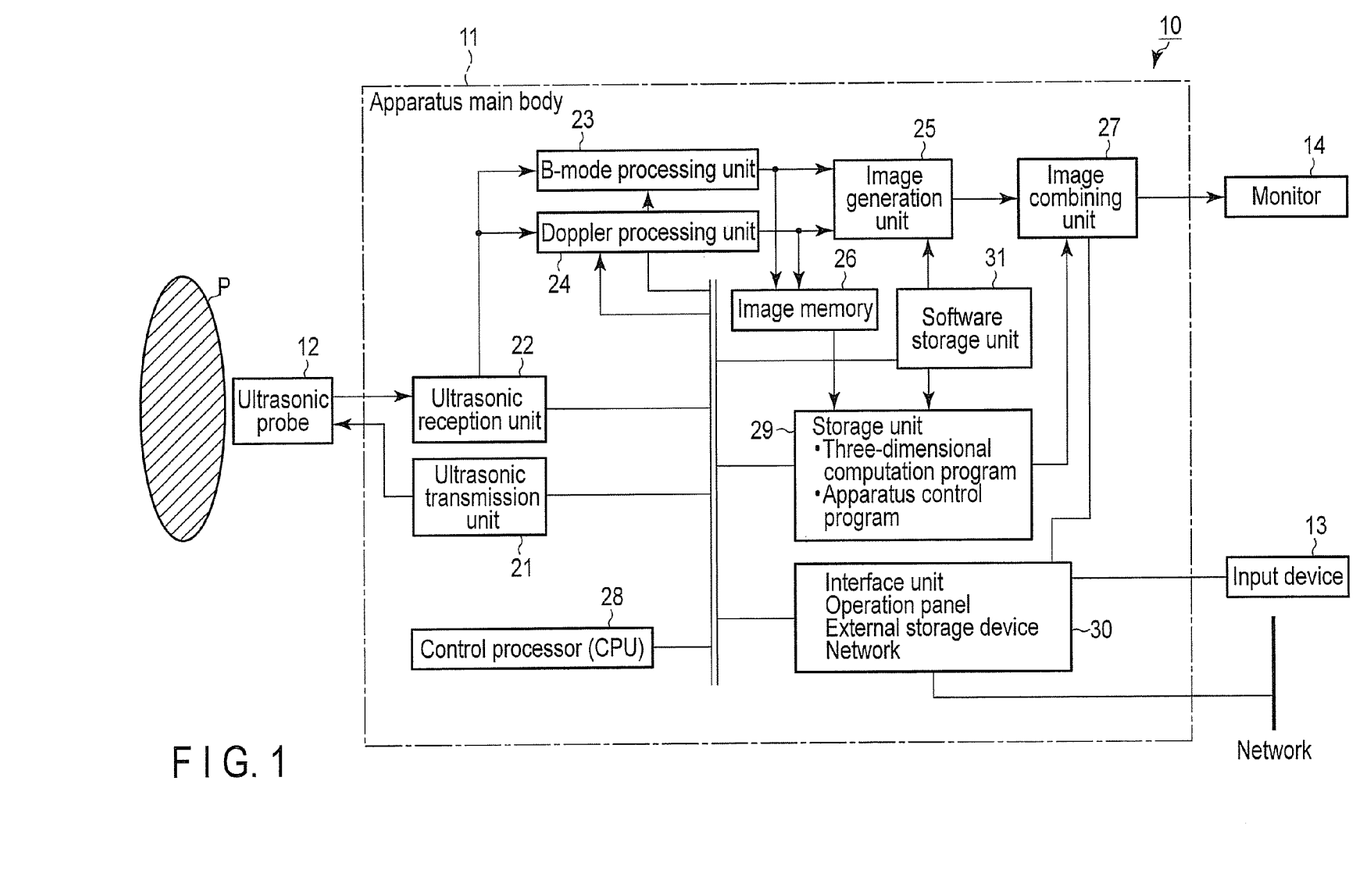
FIG. 1 is a block diagram showing the arrangement of an ultrasonic diagnostic apparatus 10 according to an embodiment.

FIG. 1 is a block diagram showing the arrangement of an ultrasonic diagnostic apparatus 10 according to this embodiment. As shown in FIG. 1, the ultrasonic diagnostic apparatus 10 includes an ultrasonic probe 12, an input device 13, a monitor 14, an ultrasonic transmission unit 21, an ultrasonic reception unit 22, a B-mode processing unit 23, a Doppler processing unit 24, an image generation unit 25, an image memory 26, an image combining unit 27, a control processor (CPU) 28, a storage unit 29, an interface unit 30, and a software storage unit 31. The ultrasonic transmission unit 21, ultrasonic reception unit 22, and the like incorporated in an apparatus body 11 are sometimes implemented by hardware such as integrated circuits and other times by software programs in the form of software modules. The function of each constituent element will be described below.

The ultrasonic probe 12 includes a plurality of piezoelectric transducers which generate ultrasonic waves based on driving signals from the ultrasonic transmission unit 21 and convert reflected waves from an object into electrical signals, a matching layer provided for the piezoelectric transducers, and a backing member which prevents ultrasonic waves from propagating backward from the piezoelectric transducers. When ultrasonic waves are transmitted from the ultrasonic probe 12 to an object P, the transmitted ultrasonic waves are sequentially reflected by the discontinuity surface of acoustic impedance of an internal body tissue, and are received as echo signals by the ultrasonic probe 12. The amplitude of such an echo signal depends on an acoustic impedance difference on the discontinuity surface by which the echo signal is reflected. The echo produced when a transmitted ultrasonic pulse is reflected by the surface of a moving blood flow, cardiac wall, or the like is subjected to a frequency shift depending on the velocity component of the moving body in the ultrasonic transmission direction due to the Doppler effect.

The input device 13 is connected to the apparatus main body 11 and includes a trackball, various types of switches, buttons, a mouse, and a keyboard which are used to input, to the apparatus main body 11, various types of instructions and conditions, an instruction to set a region of interest (ROI), various types of image quality condition setting instructions, and the like from an operator.

The monitor 14 displays morphological information and blood flow information in the living body based on video signals from the image combining unit 27.

The ultrasonic transmission unit 21 includes a trigger generation circuit, delay circuit, and pulser circuit (none of which are shown). The pulser circuit repetitively generates rate pulses for the formation of transmission ultrasonic waves at a predetermined rate frequency fr Hz (period: 1/fr sec). The delay unit gives each rate pulse a delay time necessary to focus an ultrasonic wave into a beam and determine transmission directivity for each channel. Changing this delay information can arbitrarily adjust the transmission direction from the probe transducer surface. The trigger generation circuit applies a driving pulse to the ultrasonic probe 12 at the timing based on this rate pulse.

The ultrasonic reception unit 22 includes an amplification circuit, A/D converter, and an adder. The amplification circuit amplifies an echo signal captured via the probe 12 for each channel. The A/D converter gives the amplified echo signals delay times necessary to determine reception directivities. The adder then performs addition processing for the signals. With this addition, the reflection component of the echo signal from the direction corresponding to the reception directivity is enhanced, and a composite beam for ultrasonic transmission/reception is formed in accordance with the reception directivity and transmission directivity.

The B-mode processing unit 23 receives an echo signal from the ultrasonic reception unit 22, and performs logarithmic amplification, envelope detection processing, and the like for the signal to generate data whose signal intensity is expressed by a luminance level. In this case, changing the detection frequency can change the frequency band for visualization. This arrangement also allows to concurrently perform detection processing with two detection frequencies for one reception data. Using this technique can generate a bubble image and a tissue image from one reception signal. The data processed by the B-mode processing unit 23 is output to the image generation unit 25, and is reconstructed as a B-mode image whose reflected wave intensity is expressed by a luminance.

The Doppler processing unit 24 frequency-analyzes velocity information from the echo signal received from the reception unit 22 to extract a blood flow, tissue, and contrast medium echo component by the Doppler effect, and obtains blood flow information such as an average velocity, variance, and power at multiple points. The obtained blood flow information is sent to the image generation circuit 25, and is displayed in color as an average velocity image, a variance image, a power image, and a combined image of them on the monitor 14.

Figure 2:
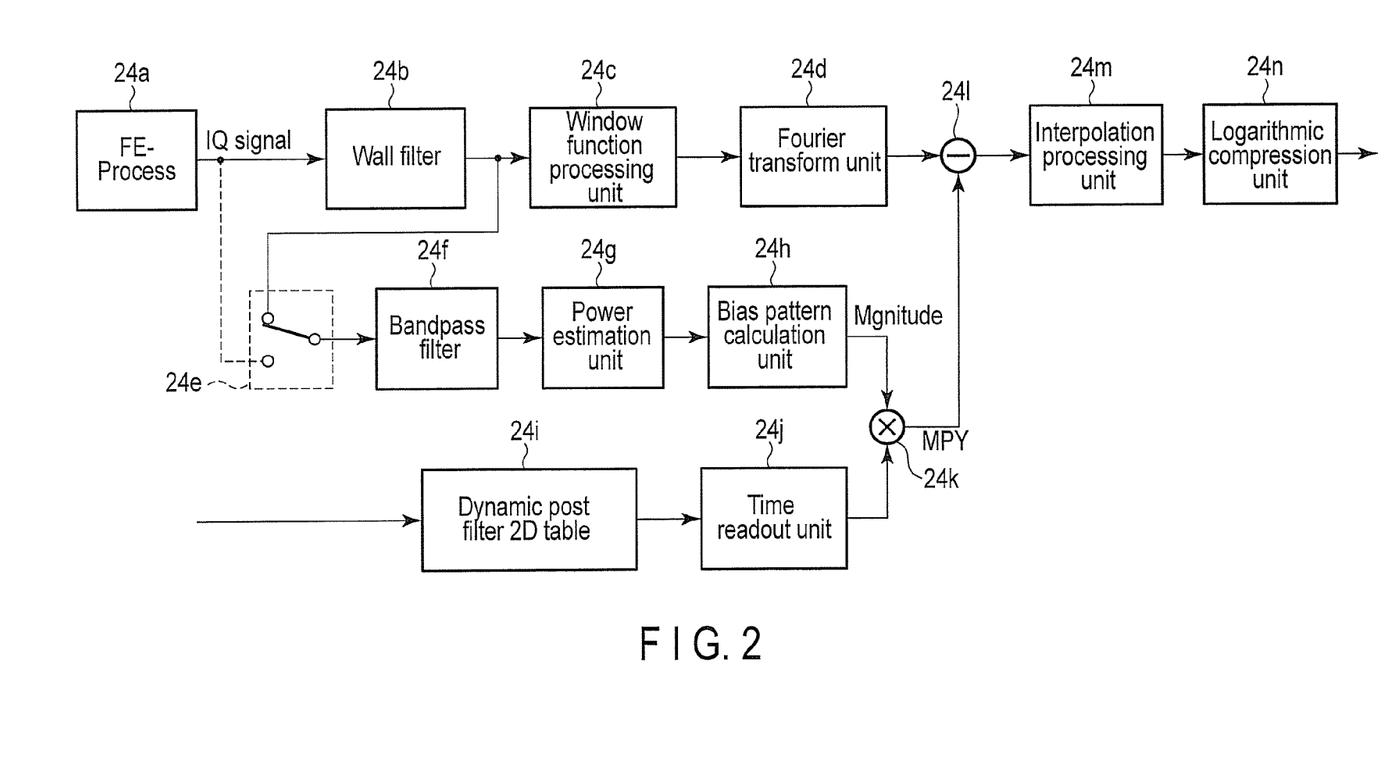
FIG. 2 is a block diagram showing an example of an arrangement provided for a Doppler processing unit 24 to implement a loss interpolation function and a transient response reduction function.

In addition, in order to implement a loss interpolation function and transient response reduction function (to be described later), the Doppler processing unit 24 includes a wall filter 24b, a window function processing unit 24c, a Fourier transform unit 24d, a bandpass filter 24f, a power estimation unit 24g, a bias pattern calculation unit 24h, a dynamic post filter 2D table 24i, a time readout unit 24j, an integrator 24k, a difference processing unit 24l, an interpolation processing unit 24m, and a logarithmic compression unit 24n, as shown in FIG. 2. The details of processing executed by each constituent element will be described later.

The image generation unit 25 generates an ultrasonic diagnostic image as a display image by converting the scanning line signal string for ultrasonic scanning into a scanning line signal string in a general video format typified by a TV format. The image generation unit 25 is equipped with a storage memory which stores image data. For example, this unit allows the operator to call up an image recorded during examination after diagnosis. The image generation unit 25 also has a function as an image processing apparatus. When constructing, for example, volume data, the image generation unit 25 constructs volume data by spatially arranging scanning line signal strings obtained by ultrasonically scanning a three-dimensional region or continuous two-dimensional regions and executing coordinate transformation, interpolation processing, and the like, as needed. The image generation unit 25 generates a predetermined three-dimensional image by executing volume rendering using the obtained volume data, MPR processing by extracting an arbitrary tomogram in the volume data, and the like. Note that each type of image processing method or the like in the image generation unit 25 may be implemented by either a software method or a hardware method.

The image memory 26 temporarily stores ultrasonic data corresponding to a plurality of frames or a plurality of volumes.

The image combining unit 27 combines the image received from the image generation unit 25 with character information of various types of parameters, scale marks, and the like, and outputs the resultant signal as a video signal to the monitor 14.

The control processor (CPU) 28 has the function of an information processing apparatus (computer) and controls the operation of the main body of this ultrasonic diagnostic apparatus. The control processor 28 reads out, from the storage unit 29, a program for implementing various types of image processing methods and programs for implementing the transient response reduction function and loss interpolation function (to be described later), expands the programs in a memory (not shown), and executes computation, control, and the like associated with each type of processing.

The storage unit 29 stores programs for executing various kinds of scan sequences, dedicated programs for implementing the transient response reduction function and loss interpolation function (to be described later), control programs for executing image generation and display processing, diagnosis information (patient ID, findings by doctors, and the like), a diagnostic protocol, transmission/reception conditions, a body mark generation program, and other data. The storage unit 29 is also used to store images in the image memory 26, as needed. It is possible to transfer data in the storage unit 29 to an external peripheral device via the interface unit 30.

The interface unit 30 is an interface associated with the input device 13, a network, and a new external storage device (not shown). The interface unit 30 can transfer, via a network, data such as ultrasonic images, analysis results, and the like obtained by this apparatus to another apparatus.

(Transient Response Reduction Function and Loss Interpolation Function)

The transient response reduction function and loss interpolation function of the ultrasonic diagnostic apparatus 10, which are used for imaging based on the CWD/B simultaneous mode, will be described next. The transient response reduction function reduces noise due to a transient response by estimating/calculating a response spectrum (two dimensions including a time domain and a frequency domain) of a transient response excited and generated by noise (e.g., direct component (DC) variations or the like caused by an analog switch) mixed due to intermittent transmission/reception upon switching between the Doppler mode and the B mode in imaging based on the CWD/B simultaneous mode, and subtracting the spectrum from the frequency analysis result. The loss interpolation function is a function of identifying a system by a parametric model using a biological signal typified by an ECG (electrocardiogram) waveform as a deterministic external input, and predicting and interpolating a loss spectrum when continuous STFT analysis is intermittently performed by using the identified system, in imaging based on the CWD/B simultaneous mode.

Obviously, it is preferable to implement both the loss interpolation function and the transient response reduction function described above in the ultrasonic diagnostic apparatus which performs the CWD/B simultaneous mode. Obviously, however, it is possible to selectively implement or operate the loss interpolation function or the transient response reduction function, as needed. In addition, the CWD/B simultaneous mode to which the loss interpolation function and the transient response reduction function are applied may be interleaved scan or segment scan.

(Transient Response Reduction Processing)

Figure 3:
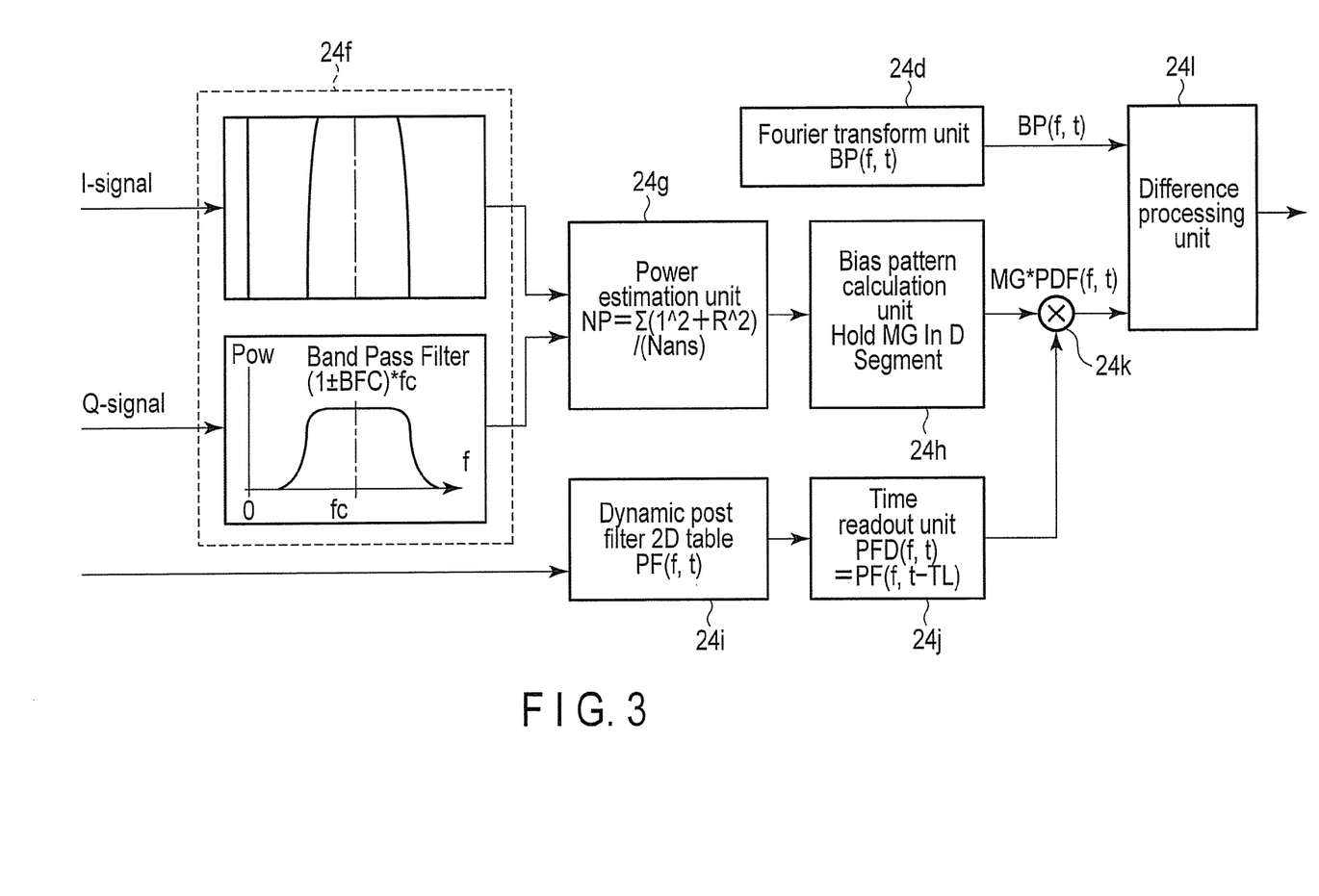
FIG. 3 is a view for explaining the operation of the Doppler processing unit 24 in transient response reduction processing.

FIG. 3 is a view for explaining the operation of the Doppler processing unit 24 in processing (transient response reduction processing) based on the transient response reduction processing. As shown in FIGS. 2 and 3, upon receiving I and Q signals from the processing unit at the end of the preceding stage, the bandpass filter 24f executes filter processing to pass only a predetermined band of each signal. The power estimation unit 24g estimates the power of a Doppler signal based on the I and Q signals after the filter processing. The bias pattern calculation unit 24h calculates a bias pattern (an STFT response generated by a transient response) at the time of switching between a B segment and a Doppler segment. Note that the calculation technique to be used is not specifically limited.

In addition, the dynamic post filter 2D table 24i dynamically selects a positive-negative symmetric simplified filter having a power dimension in response to a B mode/CWD mode switching timing signal from the control processor 28. The time readout unit 24j gives a selected simplified filter a predetermined time corresponding to a B mode/CWD mode switching timing.

The integrator 24k estimates a response spectrum component of a transient response by integrating the bias pattern calculated by the bias pattern calculation unit 24h with the post filter output from the time readout unit 24j. The difference processing unit 24l reduces a noise component (offset value) due to a transient response by subtracting the estimated response spectrum of the transient response from the spectrum component output from the Fourier transform unit 24d.

Figure 4:
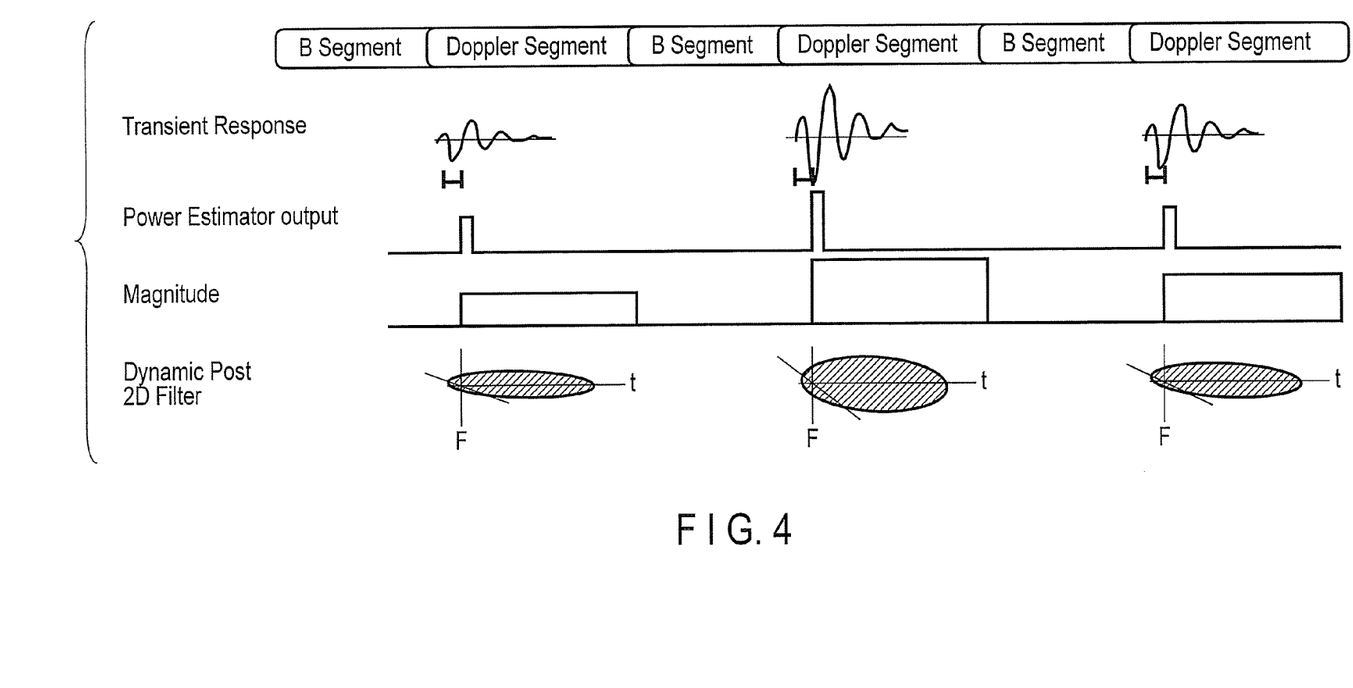
FIG. 4 is a view for explaining the execution timing of transient response reduction processing.
Figure 5:
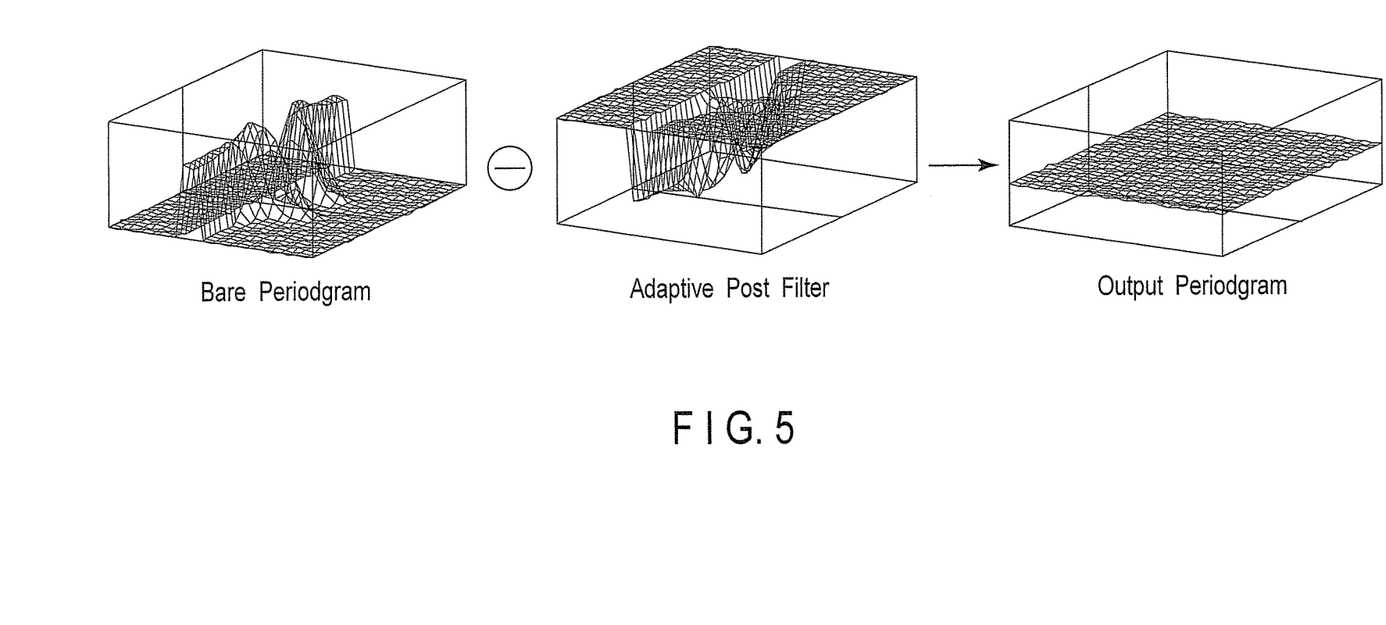
FIG. 5 is a view for explaining filter processing equivalent to transient response reduction processing.

The above transient response reduction processing is executed in CWD/B simultaneous mode imaging in accordance with an inherent transient response component generated for each switching operation from a B segment to a Doppler segment, as shown in FIG. 4. Therefore, the subtraction processing of subtracting the estimated response spectrum component of the transient response from the (bare) spectrum component detected by the CWD mode in the filter processing unit 24l is equivalent in effect to adaptive filter processing, as shown in FIG. 5.

Figure 6:
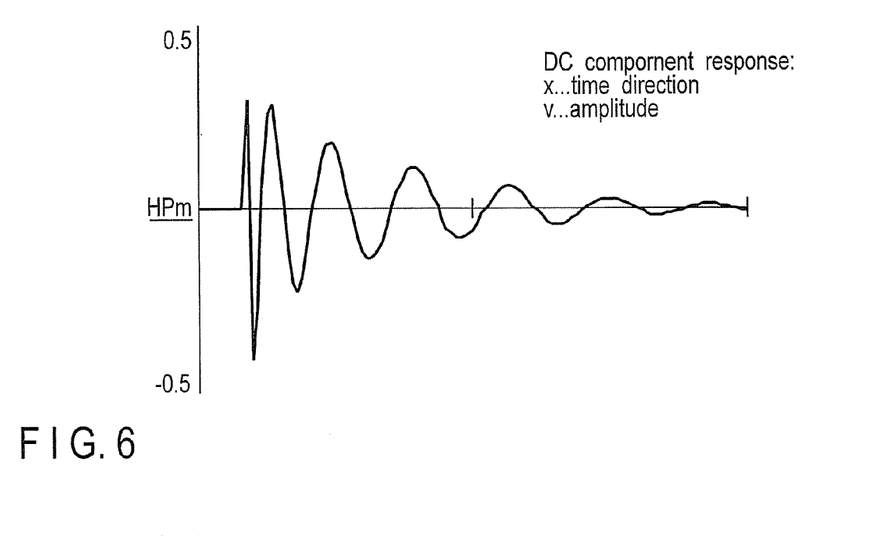
FIG. 6 is a graph for explaining a transient response.
Figure 7:
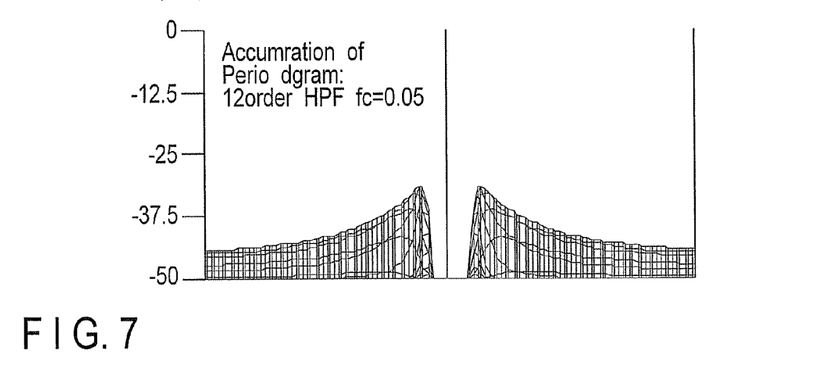
FIG. 7 is a graph showing an example of a transient response spectrum at the time when a wall filter acts.
Figure 8:
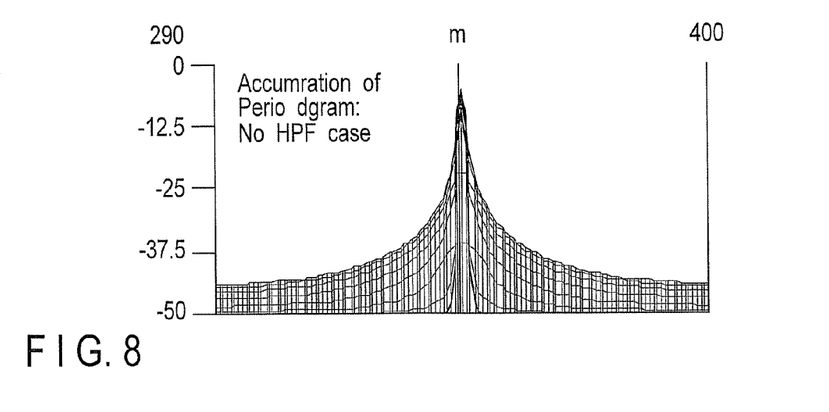
FIG. 8 is a graph showing an example of a transient response spectrum at the time when the wall filter does not act.

The above transient response reduction processing makes it possible to reduce the influence of a transient response caused by switching from the B mode to the CWD mode even if a transient response like that shown in FIG. 6 occurs due to variations in the direct current component of a received Doppler signal. The graph shown in FIG. 7, which shows temporal changes in spectrum in a superimposed state, represents a response after wall filter processing. In contrast, the graph shown in FIG. 8, which shows temporal changes in spectrum in a superimposed state, represents a response without wall filter processing. As shown in FIG. 7, the difference processing unit at the subsequent stage can implement correction by estimating the influence of the wall filter from a transient response.

(Loss Interpolation Processing)

Figure 9:
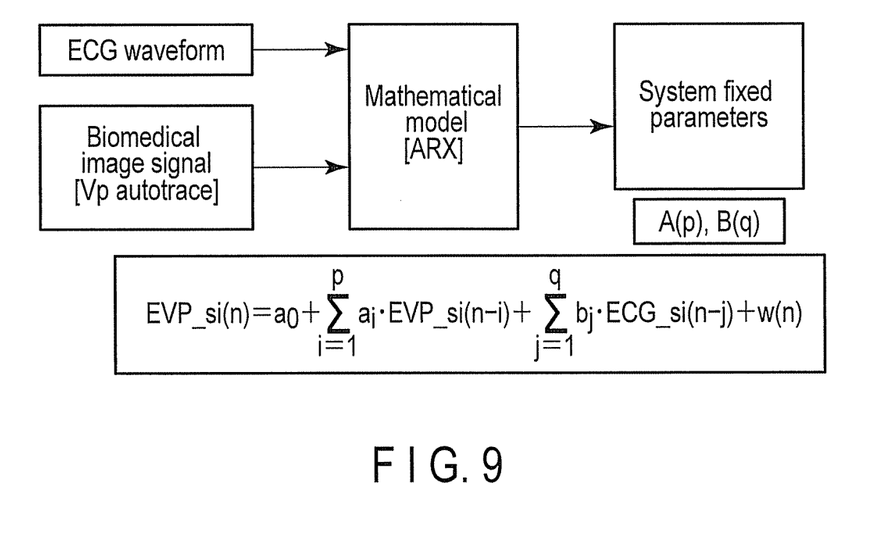
FIG. 9 is a view for explaining the concept of loss interpolation processing executed by an interpolation processing unit 24m.

FIG. 9 is a view for explaining the concept of processing (loss interpolation processing) based on the loss interpolation function executed in the interpolation processing unit 24m. As shown in FIG. 9, the interpolation processing unit 24m identifies parameters characterizing a system and a signal prediction expression $EVP\_si(n)$ by a predetermined mathematical model (parametric model) using, as inputs, an ECG waveform as an external input and a spectrum component from which an estimated response spectrum component of a transient response is subtracted. The interpolation processing unit 24m then estimates (calculates) and interpolates a lost signal by using the identified signal prediction expression EVPsi(n).

Figure 10A:
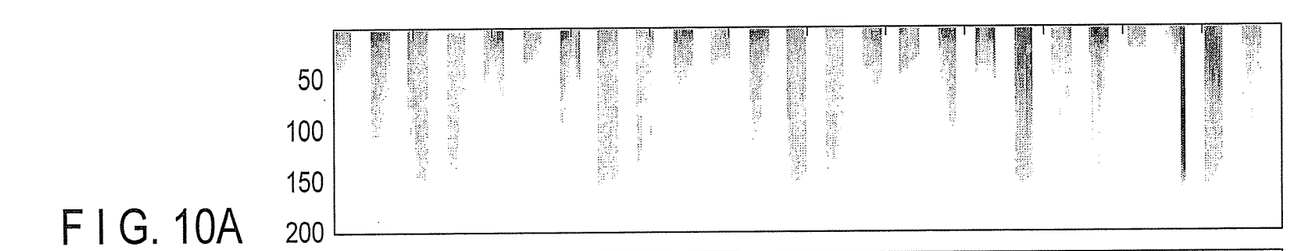
FIGS. 10A, 10B, and 10C are views for explaining the effect of loss interpolation processing.
Figure 10B:
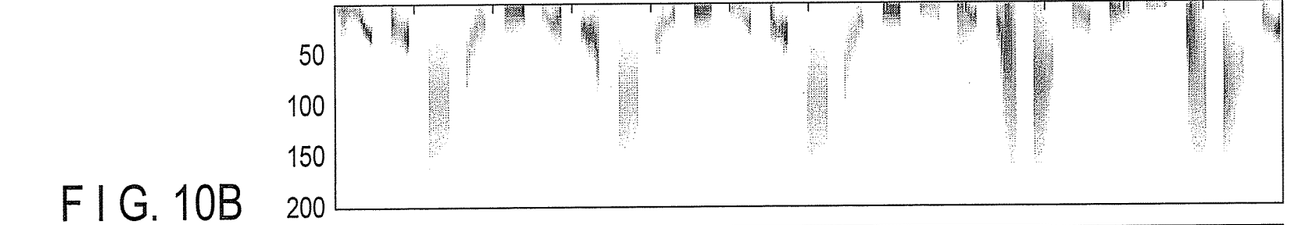
Figure 10C:
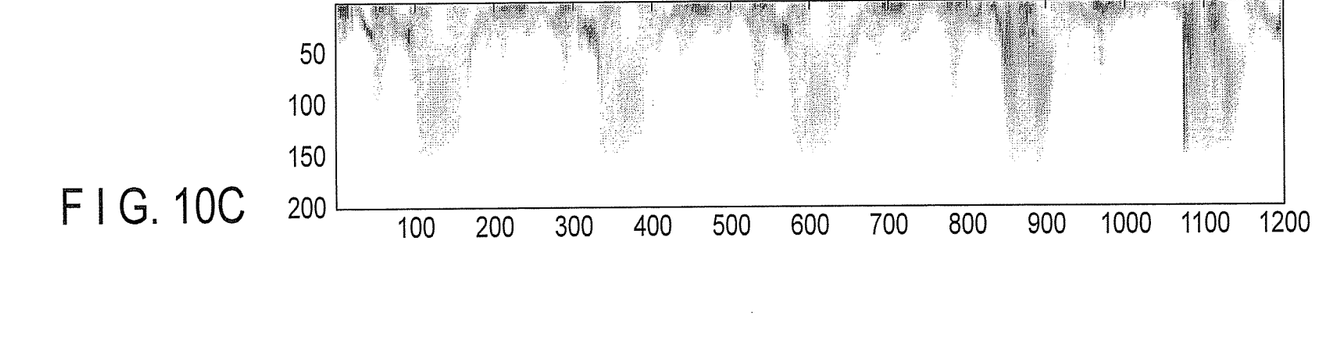

FIGS. 10A, 10B, and 10C are views for explaining the effect of loss interpolation processing. With the above loss interpolation processing, for example, interpolating a loss signal estimated as shown in FIG. 10B for a spectrum having losses as shown in FIG. 10A can acquire a Doppler spectrum with the loss portions like those shown in FIG. 10C being interpolated.

Note that such loss interpolation processing is disclosed in, for example, Jpn. Pat. Appln. KOKAI Publication No. 2001-149370. As a parametric model, it is possible to use, for example, an AR (Auto Regressive) model, ARX (Auto Regressive Exogeneous) model, ARMAX (Auto Regressive Moving Average Exogeneous) model, FIR (Finite Impulse Response) model, ARARX model, ARARMAX model, or BJ (Box and Jenkins) model.

The interpolation processing unit 24m includes a memory which temporarily stores spectrum components corresponding to a plurality of segments received from the difference processing unit 24l in chronological order. The interpolation processing unit 24m uses the spectrum components temporarily stored in the memory to execute the blend loss interpolation processing of multiplying a spectrum component corresponding to the front side (temporally past) of each loss portion and a spectrum component corresponding to the rear side (temporally future) of each loss portion by a temporally changing weighting function and adding the products. This blend loss interpolation processing can acquire a Doppler signal having smoother time continuity. Using a cosine function as a temporally changing weighting function, in particular, can efficiently reduce spike noise generated in two-dimensional spectrum responses.
(Effects)

When performing CWD/B simultaneous mode imaging, this ultrasonic diagnostic apparatus estimates/calculates a response spectrum of a transient response excited and generated by noise mixed due to intermittent transmission/reception upon switching between the Doppler mode and the B mode, and subtracts the spectrum from a frequency analysis result. This can reduce the noise component (offset value) originating from the transient response. As a consequence, the image quality in CWD/B simultaneous mode imaging can be improved.

In addition, this ultrasonic diagnostic apparatus identifies a system by a parametric model using, as inputs, an ECG waveform and the estimated response spectrum component of the transient response, and interpolates a lost signal, i.e., a Doppler signal corresponding to one B-mode frame which is lost by intermittent transmission/reception due to switching between the Doppler mode and the B mode. It is therefore possible to interpolate a lost Doppler signal when performing CWD/B simultaneous mode imaging. This can reduce the image quality deterioration caused by losses.

Second Embodiment

The first embodiment described above has exemplified the function of reducing transient responses originating from the preceding stage portion (FE) of the wall filter 24b. In practice, however, weak transient responses are generated by sampling in the wall filter 24b (for example, in the CWD mode, sampling is performed at a frequency twice that in the Fourier transform unit 24d) and sampling for frequency analysis in the window function processing unit 24c and the Fourier transform unit 24d.

This apparatus may include an arrangement for reducing transient responses generated in the wall filter 24b, the window function processing unit 24c, and the Fourier transform unit 24d in addition to or independently of the arrangement described in the first embodiment. Note that it is possible to implement the arrangement for reducing transient responses generated in the wall filter 24b, the window function processing unit 24c, and the Fourier transform unit 24d by providing a function substantially similar in effect to the transient response reduction function described in the first embodiment for each filter function.

Third Embodiment

According to the first embodiment described above, the difference processing unit 24l reduces an offset value caused by a transient response by subtracting the estimated response spectrum component of the transient response from the spectrum component output from the Fourier transform unit 24d. In contrast to this, it is possible to reduce an offset value due to a transient response on the time axis by changing the size of the offset component (the gain of a step input) using a step response waveform table of I and Q signals (2ch) before frequency analysis and subtracting the offset component from the time axis waveform before frequency analysis.

Fourth Embodiment

In general, the dynamic range at the preceding stage portion FE (Front End) of the wall filter 24b may depend on the word length (the number of bits) of an A/D converter. With the future advent of a high-speed, high dynamic range A/D converter which can output the I and Q signals immediately after the mixer and anti-alias filter or an output from the subsequent stage portion BF (Band-pass Filter), it is possible to directly calculate a response from the output and reduce a transient response component by a technique substantially similar in effect to that in the first embodiment.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus which is configured to execute an imaging mode of alternately executing a continuous wave Doppler mode of acquiring time-series continuous wave Doppler data by transmitting and receiving a continuous wave to and from an object and a B mode of acquiring tomogram data that represents luminance by transmitting and receiving a pulse wave to and from the object, the apparatus comprising:
a Doppler processing circuitry configured to
to calculate a transient response component generated due to switching between the continuous wave Doppler mode and the B mode;

to subtract the calculated transient response component from the continuous wave Doppler data to generate a remainder of the continuous wave Doppler data;

to generate Doppler spectrum information by using the remainder of the continuous wave Doppler data; and a display configured to display the Doppler spectrum information in a predetermined format.

2. The apparatus according to claim 1, wherein the Doppler processing circuitry identifies information for a system by a parametric model using a biological signal of the object as an external input, and estimates lost Doppler data due to switching between the continuous wave Doppler mode and the B mode according to the information for the system, and interpolates the continuous wave Doppler data by using the lost Doppler data.

3. The apparatus according to claim 2, wherein the Doppler processing circuitry estimates the lost Doppler data by multiplying a first spectrum component corresponding to temporal past of the lost Doppler data and a second spectrum component corresponding to temporal future of the lost Doppler data to generate products by a temporally changing weighting function and adding the products.

4. The apparatus according to claim 3, wherein the temporally changing weighting function is a cosine function.

5. The apparatus according to claim 1, wherein the Doppler processing circuitry calculates a transient response component originating from a preceding stage portion of a wall filter of the Doppler processing circuitry.

6. The apparatus according to claim 1, wherein the Doppler processing circuitry calculates a transient response component generated in a wall filter and frequency analysis circuitry of the Doppler processing circuitry.

7. The apparatus according to claim 1, wherein the Doppler processing circuitry calculates the transient response component from a spectrum having a power dimension by executing positive-negative symmetric post filter processing, and the Doppler processing circuitry subtracts the transmission component after the post filter processing from the continuous wave Doppler data having a power dimension.

8. The apparatus according to claim 1, wherein the Doppler processing circuitry calculates the transient response component as a time axis waveform by changing a magnitude of the transient response component according to a preset step response waveform table, and the Doppler processing circuitry subtracts the transient response component as the time axis waveform from the continuous wave Doppler data of the time axis waveform.

9. The apparatus according to claim 1, wherein the Doppler processing circuitry calculates the transient response component by using an output from an A/D converter of the Doppler processing circuitry.

* * * * *